United States Patent
Dishongh et al.

(10) Patent No.: US 8,120,498 B2
(45) Date of Patent: Feb. 21, 2012

(54) CAPTURING BODY MOVEMENT RELATED TO A FIXED COORDINATE SYSTEM

(75) Inventors: Terry Dishongh, Portland, OR (US);
Kofi Cobbinah, Houston, TX (US);
Karol O'Donovan, Mallow (IE);
Cliodhna Ni Scanaill, Mhuirne (IE)

(73) Assignee: Intel-GE Care Innovations LLC, Roseville, CA (US)

( * ) Notice: Subject to any disclaimer, the term of this patent is extended or adjusted under 35 U.S.C. 154(b) by 320 days.

(21) Appl. No.: 11/860,288

(22) Filed: Sep. 24, 2007

(65) Prior Publication Data

US 2009/0079559 A1 Mar. 26, 2009

(51) Int. Cl.
*G08B 23/00* (2006.01)
(52) U.S. Cl. .................... 340/573.1; 702/150
(58) Field of Classification Search ........... 340/573.1; 342/357.12, 357.14; 702/150–153; 600/595
See application file for complete search history.

(56) References Cited

U.S. PATENT DOCUMENTS

| | | | |
|---|---|---|---|
| 6,205,401 B1 | 3/2001 | Pickhard et al. | |
| 6,421,622 B1 | 7/2002 | Horton et al. | |
| 6,496,779 B1 | 12/2002 | Hwang | |
| 7,150,048 B2* | 12/2006 | Buckman | 340/573.1 |
| 2006/0049950 A1* | 3/2006 | Lockhart | 340/573.1 |
| 2007/0260418 A1* | 11/2007 | Ladetto et al. | 702/150 |
| 2008/0018532 A1* | 1/2008 | Mackintosh et al. | 342/357.12 |
| 2008/0223131 A1* | 9/2008 | Vannucci et al. | 702/153 |
| 2008/0262772 A1* | 10/2008 | Luinge et al. | 702/94 |
| 2008/0284650 A1* | 11/2008 | MacIntosh et al. | 342/357.14 |
| 2009/0204031 A1* | 8/2009 | McNames et al. | 600/595 |

FOREIGN PATENT DOCUMENTS

WO 2009/042390 A1 4/2009

OTHER PUBLICATIONS

International Search Report for PCT Patent Application No. PCT/US2008/75723, Mailed Jan. 15, 2009. 11 Pages.
Lee, Seon-Woo, et al., "Detection of Spatiotemporal Gait Parameters", Proceedings of the 2005 IEEE Engineering in Medicine and Biology 27th Annual Conference Shanghai, China Sep. 1-4, 2005, 4 pgs.
Veltink, P.H., et al., "Three dimensional inertial sensing of foot movements for automatic tuning of a two-channel implantable drop-foot stimulator", Medical Engineering & Physics 25 (2003) 21-28; www.elsevier.com/locate/ medengphy, Published 2002, 8 pgs.
Winter, David A., et al., "Biomechanics and Motor Control of Human Movement", Second Edition, N.Y. Ch. 2.10 Kinematic Conventions, Fig. 2.1, 1990, p. 13.
PCT/US2008/075723, International Preliminary Report on Patentability, Apr. 1, 2010, 6 pages.

* cited by examiner

*Primary Examiner* — John A Tweel, Jr.
(74) *Attorney, Agent, or Firm* — Pillsbury Winthrop Shaw Pittman, LLP

(57) ABSTRACT

Briefly, in accordance with one or more embodiments, a kinematic sensor may be carried by or on one or more body segments of a user to obtain one or more kinematic variables based at least in part on movement of the user with respect to a fixed, global reference system. The kinematic sensor comprises a tri-axial accelerometer sensor, a gyroscope sensor, and a magnetometer sensor to define the global reference system and to obtain kinematic data. The kinematic data may be transmitted via a wireless link to a remote information handling system or device, for example to monitor a health status of the user based at least in part on movement of the user with respect to the fixed, global reference system.

20 Claims, 6 Drawing Sheets

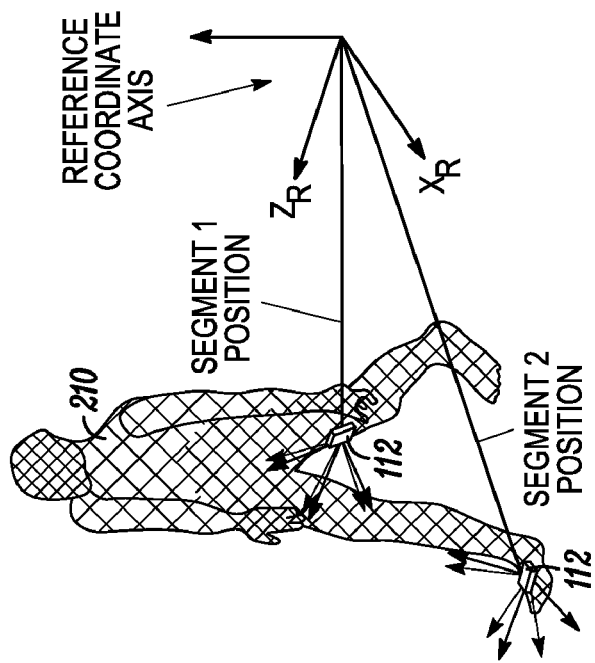
FIG. 3C
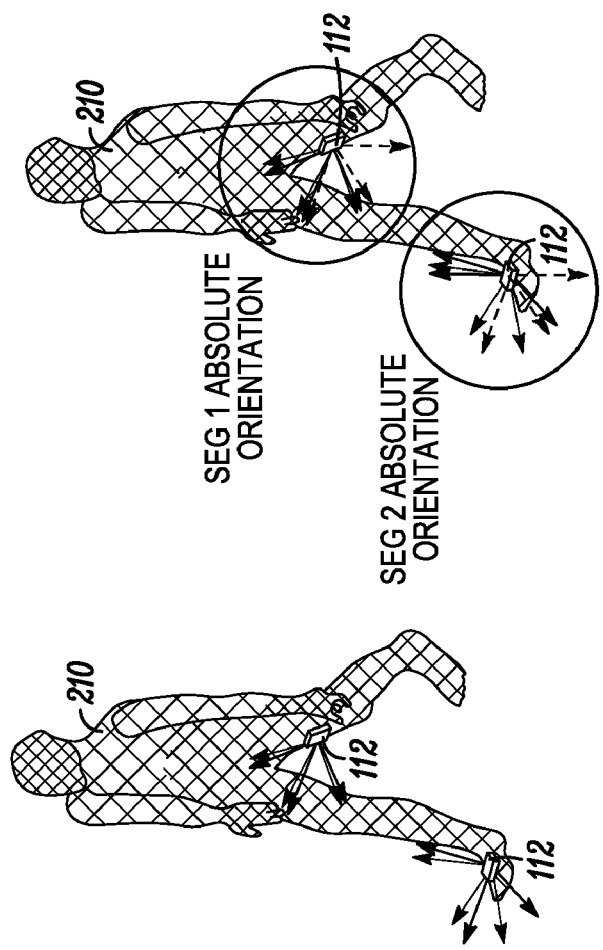
FIG. 3B
FIG. 3A

CAPTURING BODY MOVEMENT RELATED TO A FIXED COORDINATE SYSTEM

BACKGROUND

Techniques have been developed for the measurement of foot orientation and position during the swing phase of gait using a tri-axial accelerometer and gyroscope inertial monitoring units (IMU) placed on the foot, however such work has been concerned primarily with foot movement in the medial-lateral and cranial-caudal direction during the swing phase and not with distance or the direction travelled. Other techniques for measuring stride length using a tri-axial gyroscope, accelerometer and magnetometer sensor configuration with one placed on the leg and another placed on the thigh to measure stride length, however such a technique requires the length of both the upper leg and lower leg to be known.

DESCRIPTION OF THE DRAWING FIGURES

Claimed subject matter is particularly pointed out and distinctly claimed in the concluding portion of the specification. However, such subject matter may be understood by reference to the following detailed description when read with the accompanying drawings in which:

Figure 4:
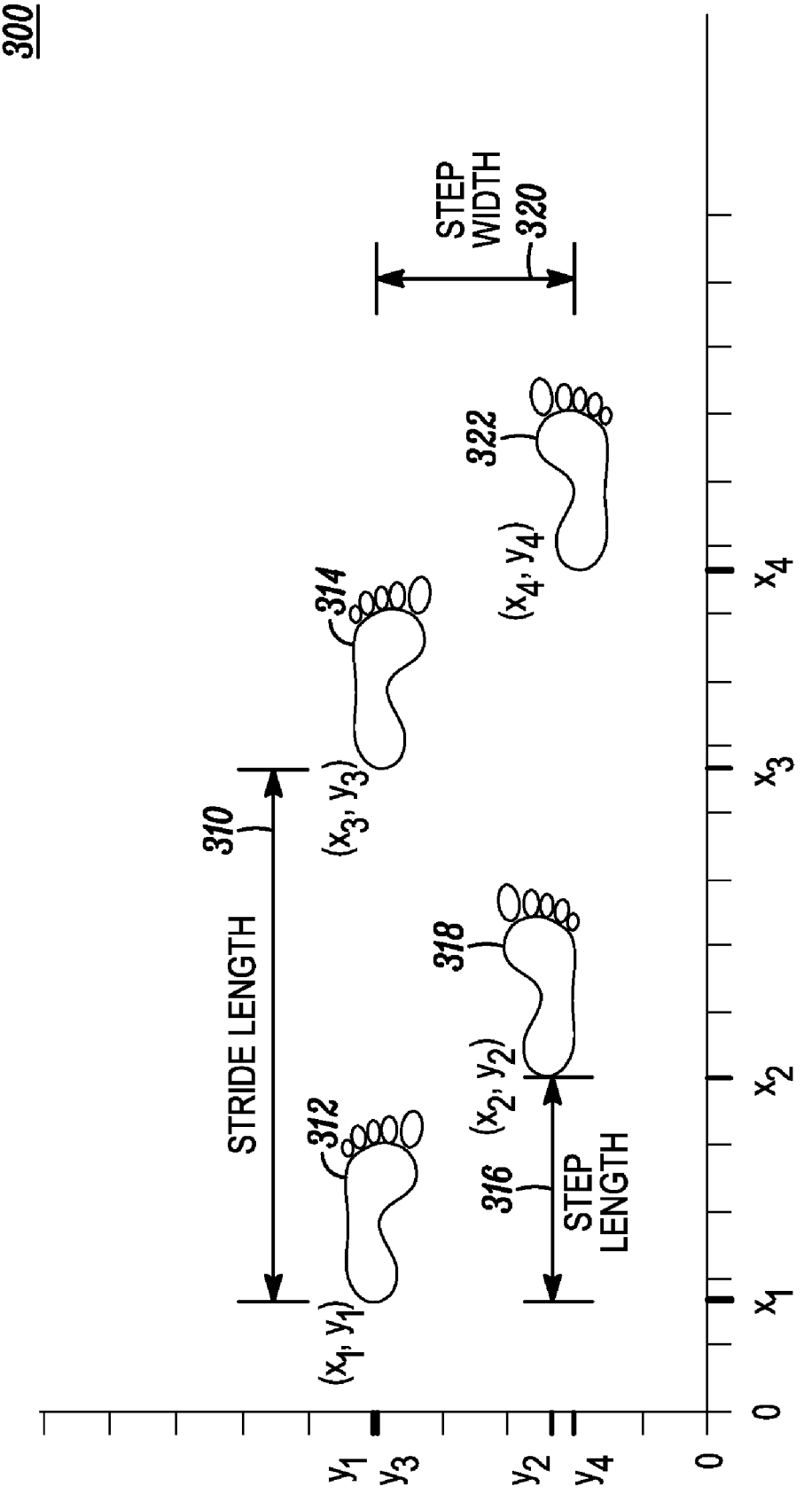
Figure 5:
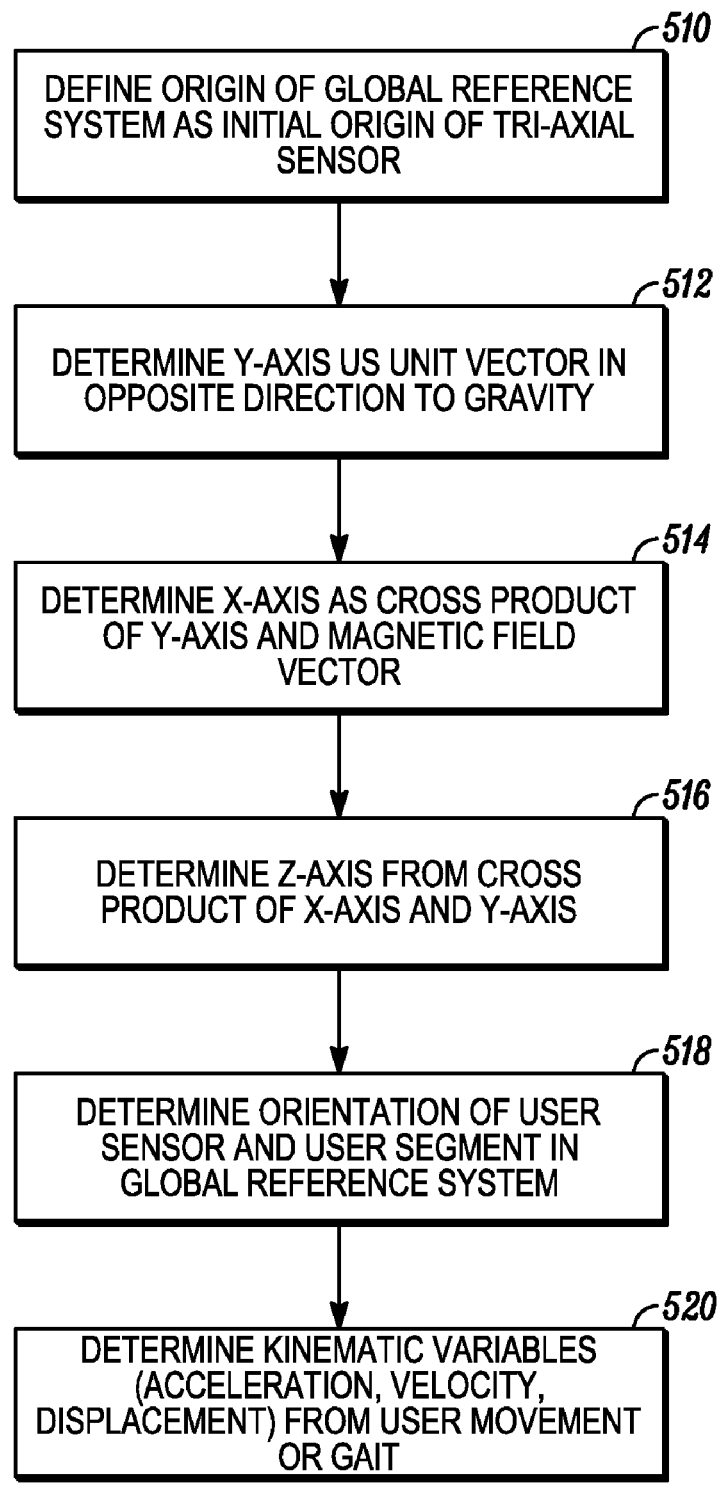
Figure 6:
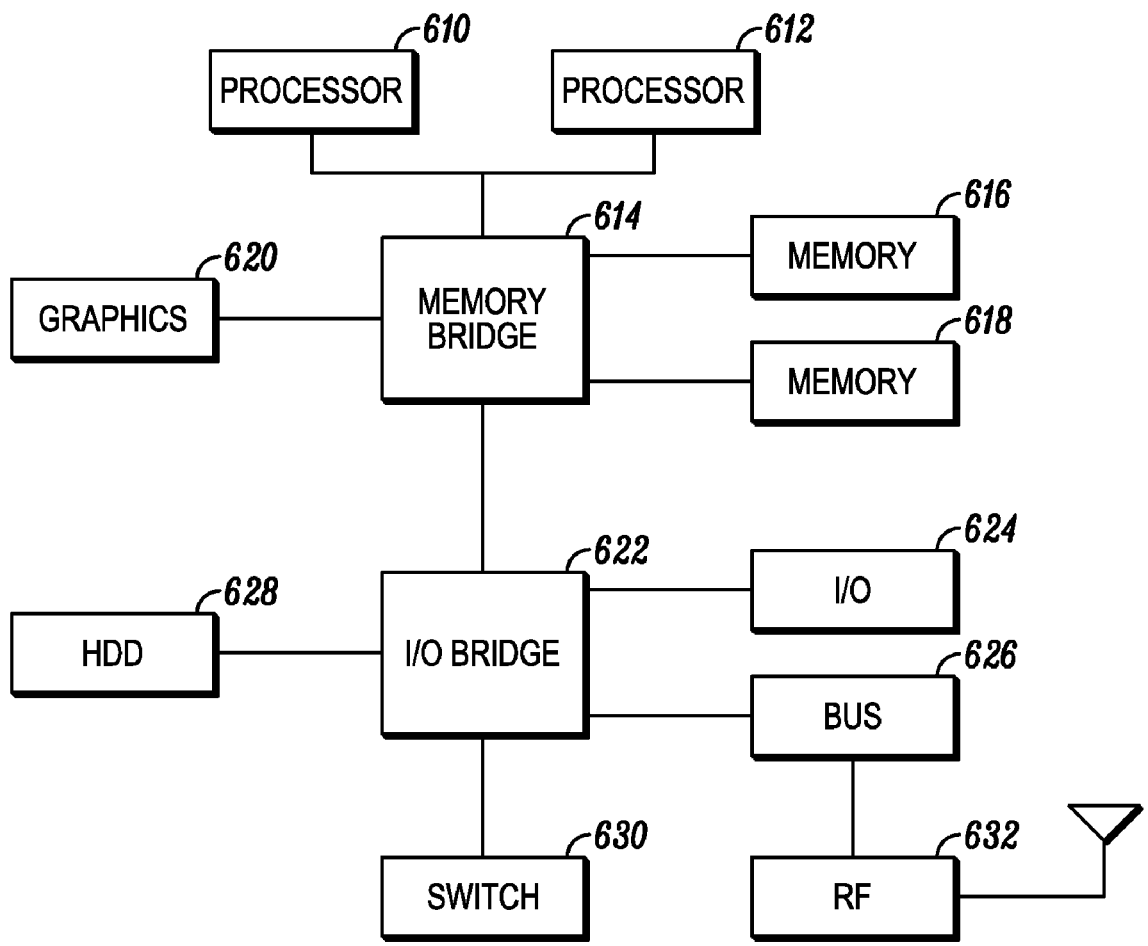

FIGS. 3A, 3B, and 3C are diagrams of coordinate axes of a sensor, orientation relative to a reference coordinate axes, and position relative to a reference coordinate axis in accordance with one or more embodiments;

FIG. 4 is a diagram referencing locations of footfalls of a user to a fixed coordinate system in accordance with one or more embodiments;

FIG. 5 is a flow diagram of a method to capture body movement related to a fixed coordinate system in accordance with one or more embodiments; and FIG. 6 is a diagram of an information handing system capable of capturing capture body movement related to a fixed coordinate system in accordance with one or more embodiments.

It will be appreciated that for simplicity and/or clarity of illustration, elements illustrated in the figures have not necessarily been drawn to scale. For example, the dimensions of some of the elements may be exaggerated relative to other elements for clarity. Further, if considered appropriate, reference numerals have been repeated among the figures to indicate corresponding and/or analogous elements.

DETAILED DESCRIPTION

In the following detailed description, numerous specific details are set forth to provide a thorough understanding of claimed subject matter. However, it will be understood by those skilled in the art that claimed subject matter may be practiced without these specific details. In other instances, well-known methods, procedures, components and/or circuits have not been described in detail.

In the following description and/or claims, the terms coupled and/or connected, along with their derivatives, may be used. In particular embodiments, connected may be used to indicate that two or more elements are in direct physical and/or electrical contact with each other. Coupled may mean that two or more elements are in direct physical and/or electrical contact. However, coupled may also mean that two or more elements may not be in direct contact with each other, but yet may still cooperate and/or interact with each other. For example, "coupled" may mean that two or more elements do not contact each other but are indirectly joined together via another element or intermediate elements. Finally, the terms "on," "overlying," and "over" may be used in the following description and claims. "On," "overlying," and "over" may be used to indicate that two or more elements are in direct physical contact with each other. However, "over" may also mean that two or more elements are not in direct contact with each other. For example, "over" may mean that one element is above another element but not contact each other and may have another element or elements in between the two elements. Furthermore, the term "and/or" may mean "and", it may mean "or", it may mean "exclusive-or", it may mean "one", it may mean "some, but not all", it may mean "neither", and/or it may mean "both", although the scope of claimed subject matter is not limited in this respect. In the following description and/or claims, the terms "comprise" and "include," along with their derivatives, may be used and are intended as synonyms for each other.

Figure 1:
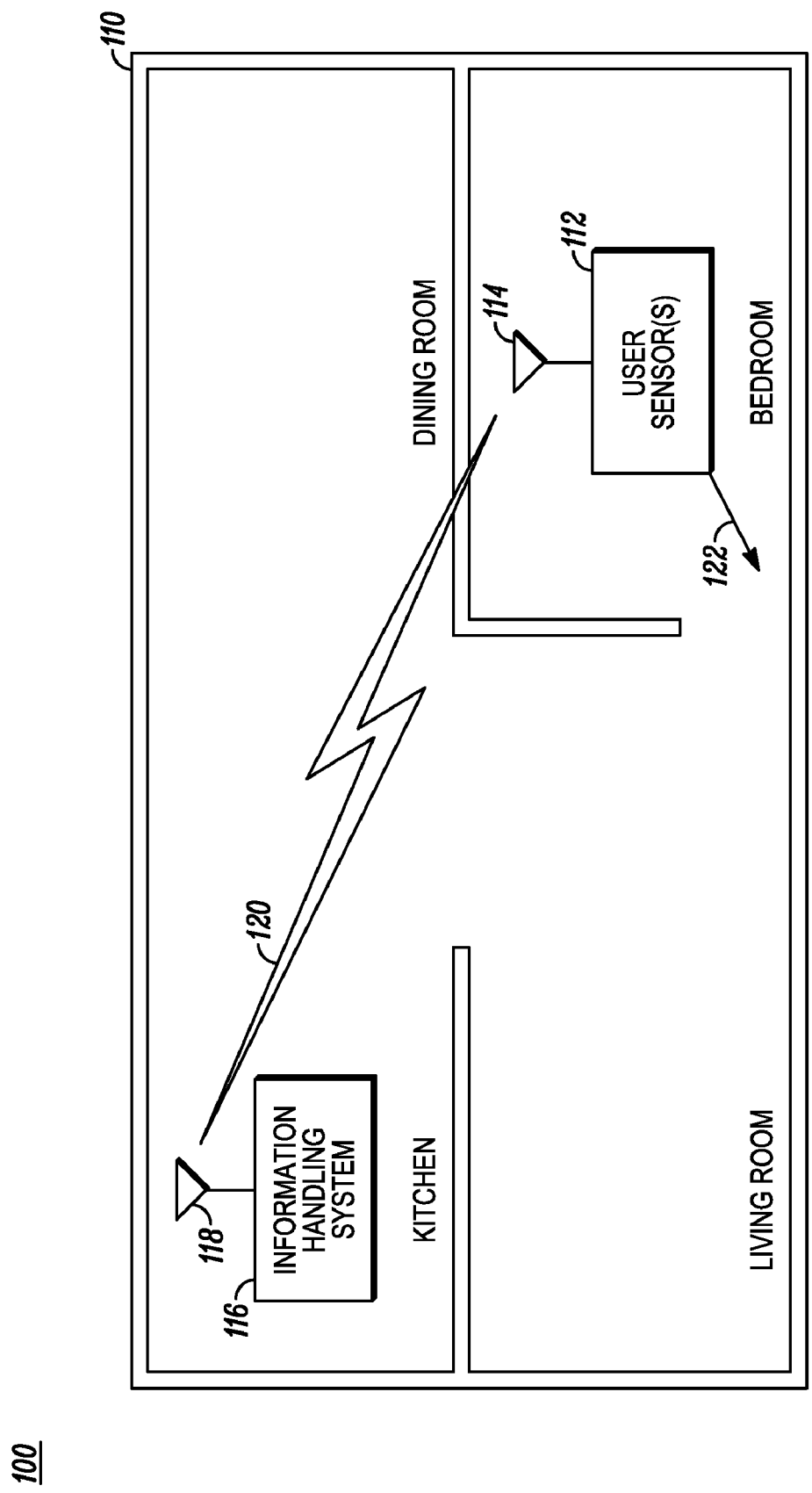
FIG. 1 is a diagram of a local area network disposed in a building such as a house to capture body movement related to a fixed coordinate system in accordance with one or more embodiments.

Referring now to FIG. 1, a diagram of a local area network disposed in a building such as a house to capture body movement related to a fixed coordinate system in accordance with one or more embodiments will be discussed. As shown in FIG. 1, network 100 may comprise a local area network (LAN) disposed in a building 110 which may comprise, for example, a home or other structure that may have unique, or nearly unique, architectural features and/or layout. For example, building 110 may comprise a kitchen area, a dining room area, a living room area, and/or a bedroom area. In one or more embodiments, network 100 may include information handling system 116 that includes antenna 118 to couple to one or more user sensors 112 likewise having an antenna 114 so that information handling system 116 may communicate with one or more user sensors 112 via wireless link 120. In one or more embodiments, communication via wireless link 120 on network 100 may be in compliance with an Institute of Electrical and Electronics Engineers (IEEE) standard, for example an IEEE 802.11 a/b/g/n standard or the like. Alternatively, communication via wireless link 120 on network 100 may be in compliance with a Bluetooth standard or an Ultra Wide Band (UWB) standard or the like, and the scope of the claimed subject matter is not limited in this respect. In one or more embodiments, user sensor 112 may comprise at least a tri-axial accelerometer sensor, a gyroscope sensor, and a magnetometer sensor. One or more such user sensors 112 may be attached to one or more segments of the user, for example a foot, a calf, and/or a thigh of a user, to obtain kinematic data due to the movement and/or gait of the user as the user moves throughout building 110. By using such an arrangement of sensors in the one or more user sensors 112, the relative position of one or more segments of the user with respect to a single, fixed coordinate axis may be determined from which kinematic data such as gait parameters, for example step width, step length, stride length, and time and/or speed of such movements, may be determined, for example to monitor the health condition of the user, although the scope of the claimed subject matter is not limited in this respect.

In one or more embodiments, network 100 comprises a wireless system that is capable of avoiding impeding the natural motion of a user and is capable of capturing limb movement of the user independent of placement of the one or more user sensors 112 and/or orientation thereof. In one or more embodiments, the variables of network 100 are measured with respect to a fixed reference coordinate system, for example as shown in and described with respect to FIG. 2, below to implement gait capture via inertial and/or magnetic sensors disposed in the one or more user sensors 112 to determine gait parameters with respect to the fixed reference coordinate axis. Such an arrangement allows for the determination of step length and/or step width of the user without requiring additional sensors for measuring additional forces. An example fixed reference coordinate system is discussed with respect to FIG. 2, below.

Figure 2:
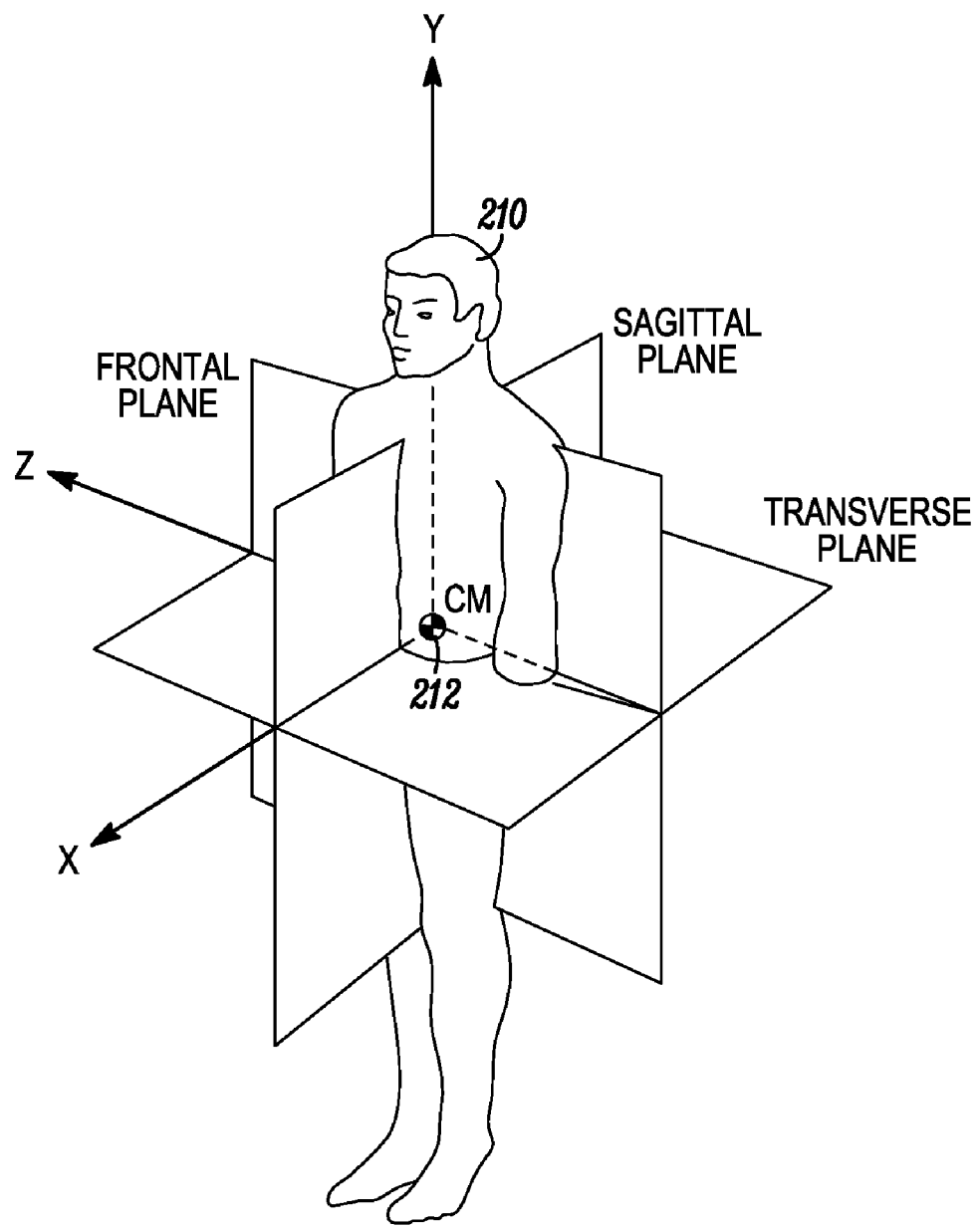
FIG. 2 is a diagram of a global spatial reference system utilized to determine one or more measurements of a user in accordance with one or more embodiments.

Referring now to FIG. 2, a diagram of a global spatial reference system utilized to determine one or more measurements of a user in accordance with one or more embodiments will be discussed. In the study of kinematics, a coordinate axis system can be either relative in which all coordinates are relative to an anatomical location which changes from segment to segment, or global in which all coordinates are relative to an external spatial system. Variables such as displacement, velocity, acceleration and/or angular measurements may also be relative or global. In one or more embodiments, an analysis of movement of one segment relative to another, which is utilized to determine step length and/or step width, by establishing a global spatial reference system 200 as shown in FIG. 2.

A global spatial reference system 200 in accordance with a recommendation of the Institute of Systems Biology (ISB) of Seattle, Washington, USA, is depicted in FIG. 2. Such a global spatial reference system 200 is discussed in Winter, D. A. *Biomechanics and Motor Control of Human Movement*, Second Edition, N.Y., Wiley, 1990. According to such a convention, angles in the sagittal plane are measured from zero degrees in the X direction with positive angles being counter-clockwise. Similarly, angles in the frontal plane are measured from zero degrees in the Y direction and increase positively counter-clockwise, and angles in the transverse plane are measured from zero degrees in the Z direction and increase positively counter-clockwise. The center of all three axes defining origin 212 optionally, but not necessarily, may be disposed at a center of mass (CM) of a user 210 such that an orientation of user 210 may be measured, for example the position of the feet of the user in reference system 200. Examples of how the orientation and/or position of user 210 with respect to reference system are discussed with respect to FIGS. 3A, 3B, and 3C, below.

Referring now to FIGS. 3A, 3B, and 3C, diagrams of coordinate axes of a sensor, orientation relative to a reference coordinate axes, and position relative to a reference coordinate axis in accordance with one or more embodiments will be discussed. In one or more embodiments, user sensor 112 comprises one or more Inertial Monitoring Units (IMU) be disposed in and/or on the body of user 210. Such an inertial monitoring unit comprises a self contained sensor unit consisting of a tri-axial accelerometer, gyroscope and/or magnetometer sensor arrangement. User sensor 112 is capable of transmitting real-time clock (RTC) time stamped inertial data via wireless link 120 from user sensor 112 to information handling system which may be, for example, a local personal computer disposed in building 110. The inertial monitoring units are capable of measuring acceleration, angular velocity and/or direction with respect to a magnetic field vector in three dimensions. Using such data, the position and/or orientation of given user sensor 112 relative to a global reference system 200 may be determined, which thereby allows information handling system 116 to determine the arrangement of the various user sensors 112 relative to one another. Gait parameters for user 210 describing acceleration, velocity, and/or displacement can then be extracted using global referencing system 200. The timing of gait events may also be extracted from the real-time clock time stamped data.

In one or more embodiments, global reference system 200 may be determined using data from the one or more user sensors 112. The reference coordinate axes in global referencing system 200 may be established as follows. First, user sensors 112 are fixed to the segment, and the orientation of the segment coordinate axis with respect to the coordinate axis of user sensor 112 is determined using a simple two stage procedure as shown in FIG. 3A. Then the orientation of the reference coordinate axis with respect to the coordinate axis of user sensor 112 may be determined as follows as shown in FIG. 3B. This involves determining the y-axis, as the unit vector in the opposite direction to gravity, determining the x-axis, the cross product of the y-axis and the magnetic field vector, and determining the z-axis, from the cross product of the y-axis and the x-axis. Position vectors may be calculated from the double integration of the acceleration vector when the gravity vector is subtracted as shown in FIG. 3A. When using inertial sensors such as user sensors 112 to determine kinematic variables for gait analysis, a reference coordinate axis is established from which the orientation and position of the segment may be determined.

The origin 212 of the reference coordinate axis may be determined as the location of the origin of the coordinate axis of the tri-axial sensor at the instance that the reference axis is defined, for example the beginning of the period of interest. An initial step width of zero may be assumed from a starting position. Next, the y-axis of the reference coordinate axis may be defined. A tri-axial accelerometer may be formed via three orthogonal measuring axes. A three-dimensional acceleration vector may be obtained from a tri-axial accelerometer. This acceleration vector may be measured by a tri-axial accelerometer written in array format and may be given by the following equation (Equation 1):

$$\hat{a}_T = \begin{vmatrix} a_{Tx} \\ a_{Ty} \\ a_{Tz} \end{vmatrix} = \begin{vmatrix} a_I \cos(\theta_x) + g \cos(\phi_x) \\ a_I \cos(\theta_y) + g \cos(\phi_y) \\ a_I \cos(\theta_z) + g \cos(\phi_z) \end{vmatrix}$$

where
$a_T$ is the measured acceleration vector;
$a_1$ is the magnitude of the inertial acceleration vector;
$\theta$ is the inclination of the measuring axis with respect to the inertial acceleration vector;
g is the magnitude of the gravitational acceleration vector; and
$\Phi$ is the inclination of the measuring axis with respect to the vertical axis (gravity vector).

The y-axis of the reference coordinate axis may be defined as a unit vector in the opposite direction to the gravity vector. From Equation 1, under static conditions, that is no inertial acceleration, the acceleration is given by Equation 1. Equation 2 defines the gravity vector:

$$^{SEN}\hat{a}_T = {}^{SEN}\begin{vmatrix} a_{Tx} \\ a_{Ty} \\ a_{Tz} \end{vmatrix} = {}^{SEN}\begin{vmatrix} g \cos(\phi_x) \\ g \cos(\phi_y) \\ g \cos(\phi_z) \end{vmatrix} = {}^{SEN}\hat{g}$$

where the superscript SEN indicates the variable is measured in the sensor coordinate axis. Under static conditions a tri-axial accelerometer can thus be used to determine in three dimensional coordinates the direction of the gravity vector within the sensor coordinate axis. During dynamic activity the gravity vector may not be able to be determined accurately using accelerometers alone because the accelerometer signal also contains the inertial acceleration signal, although the scope of the claimed subject matter is not limited in this respect.

During dynamic activity the tri-axial rate gyroscope signal may be integrated to determine the change in orientation of a segment. Due to the non-commutative behavior of rotational mathematics an integration technique known as strap-down integration may be utilized. The gravity vector can thus be tracked during dynamic activity by mapping the vector determined by the accelerometers during static periods using the change in orientation determined using the gyroscopes. The direction of the gravity vector, and hence the y-axis of the reference coordinate axis, can thus be determined through all of time (Equation 3):

$$_{REF}^{SEN}\hat{y} = \frac{^{SEN}\hat{g}}{|^{SEN}\hat{g}|}$$

Next, the x-axis of the reference coordinate axis may be defined. A tri-axial magnetometer may be formed by three orthogonal measuring axes. A three-dimensional magnetic field vector may be obtained from a tri-axial magnetometer. The magnetic field vector measured by a tri-axial magnetometer written in array format is given as follows (Equation 4):

$$\hat{m} = \begin{vmatrix} m\cos(\beta_x) \\ m\cos(\beta_y) \\ m\cos(\beta_z) \end{vmatrix}$$

where
$\hat{m}$ is the measured magnetic field vector;
$\beta$ is the inclination of the measuring axis with respect to the magnetic field vector; and
m is the magnitude of the magnetic field vector.

The x-axis of the reference coordinate axis is calculated as the normalized cross product of magnetic field vector and the y-axis (Equation 5):

$$_{REF}^{SEN}\hat{x} = {_{REF}^{SEN}\hat{y}} \times {^{SEN}\hat{m}}$$

Next, the z-axis of the reference coordinate axis may be defined. The z-axis of the reference coordinate axis is easily determined from the cross product of the y-axis and the x-axis (Equation 6):

$$_{REF}^{SEN}\hat{z} = {_{REF}^{SEN}\hat{y}} \times {_{REF}^{SEN}\hat{x}}$$

Next, the segment orientation within the reference coordinate axis may be defined. Once the three axes of the reference coordinate axis have been defined within the sensor coordinate axis its orientation with respect to the sensor coordinate axis $$_{REF}^{SEN}R$$

is given by (Equation 8):

$$_{REF}^{SEN}R = \lfloor {_{REF}^{SEN}\hat{x}} \quad {_{REF}^{SEN}\hat{y}} \quad {_{REF}^{SEN}\hat{z}} \rfloor$$

The orientation of the sensor axis within the respect to the reference coordinate axis is easily calculated as the inverse (Equation 9):

$$_{SEN}^{REF}R = ({_{REF}^{SEN}R})^{-1}$$

The orientation of the segment coordinate axis with respect to the sensor coordinate axis is given by $$_{SEG}^{SEN}R \cdot {_{SEG}^{SEN}R}$$

may be known if the sensor is attached to the segment at a pre-defined position or alternatively it may be calculated using a simple two step procedure once the sensor unit is attached to the segment. The orientation of the segment with respect to the reference coordinate axis, $$_{SEG}^{REF}R,$$

is then given by (Equation 10):

$$_{SEG}^{REF}R = {_{SEN}^{REF}R} \cdot {_{SEG}^{SEN}R}$$

Next, one or more kinematic variables may be determined. Once the orientation of the segment within the reference coordinate axis has been established all angular data may be calculated from the $$_{SEG}^{REF}R$$

orientation matrix and its time derivatives. Linear acceleration, velocity and displacement are calculated as follows. If the gravity vector which is determined as outlined, above, is subtracted from the acceleration as defined by Equation 1, the inertial acceleration can be determined as follows (Equation 11):

$$^{SEN}\hat{a}_I = {^{SEN}}\begin{vmatrix} a_{Ix} \\ a_{Iy} \\ a_{Iz} \end{vmatrix} = {^{SEN}\hat{a}_T} - {^{SEN}\hat{g}}$$

The velocity vector $\hat{v}$ may be calculated by integration of the inertial acceleration (Equation 12):

$$\hat{v} = \int \hat{a} \cdot dt$$

Similarly, the distance traveled, or direction of progression, $\hat{s}$ may be calculated by double integration of the acceleration signal (Equation 13):

$$S = \int \hat{v} \cdot dt = \iint \hat{a} \cdot dt^2$$

Referring now to FIG. 4, a diagram referencing locations of footfalls of a user to a fixed coordinate system in accordance with one or more embodiments will be discussed. In one or more embodiments, the gait of user 210 may be captured by relating kinematic user sensors 112 to a global reference system 200 without requiring the use of secondary data capture. In such an arrangement, utilization of a global reference system 200 enables the measurement of step length and step width between two feet of user 210, and which further may be combined with the real-time clock (RTC) time stamped data to calculate step time. Thus, as shown in diagram 300 of FIG. 4, as user 210 walks in a plane defined by X axis and Y axis of global reference system 200, user sensors 112 may capture the stride length 310 of user 210 which may be defined as the distance between two consecutive steps 312 and 314 of the same foot of user 210. Likewise, user sensors 112 may capture the step length 316 of user 210 which may be defined distance between two consecutive steps 312 and 318 of opposite feet of user 210 measured in the direction of movement of user 210. In addition, user sensors 112 may capture the step width 320 of user 210 which may be defined as the distance between two consecutive steps 314 and 322 of opposite feet of user 210 measured in a direction generally normal to the direction of movement of user 210. The captured stride length data and/or the captured step length data may be combined with RTC time data to determine the speed and/or velocity of movement of user 210. Such an arrangement may be utilized to determine the position and orientation of the foot/shank/thigh segment of user 210. In one or more embodiments, user sensor 112 may comprise a tri-axial accelerometer, gyroscope and/or magnetometer arrangement attached to one or more segments of interest, for example a foot of user 210, a thigh of user 210, and so on. The arrangement of user sensors 112 and information handling system 116 provides the ability to determine relative position of the segments of user 210 with respect to a single reference coordinate axis 200. Such an arrangement allows for the determination of critical gait parameters such as step width and step length which in addition to step time were previously incapable of being undetermined using inertial motion unit sensors, although the scope of the claimed subject matter is not limited in this respect.

By monitoring the movement of user 210 as described, the health of user 210 may be monitored, for example via software running on information handling system 116 and/or running on a remote device coupled to information handling system 116 via a network such as the Internet. Likewise, a healthcare professional is capable of monitoring the health of user 210 by observing real time, or near real time, movement and/or gait data captured by user sensors 112 and/or information handling system 116. Alternatively, such movement and/or gait data may be batched and stored in one or more user sensors 112, information handling system 116 or a remote device coupled to information handling system 116 via a network, and periodically or occasionally monitored by the healthcare professional. In the event an anomaly in the movement and/or gait of user 210 is observed or detected, appropriate action may be taken if needed, although the scope of the claimed subject matter is not limited in this respect. In one or more embodiments, one or more of user sensor 112 and/or information handling system 116 may comprise a platform architecture, at least in part, as shown in and described with respect to FIG. 6, below.

Referring now to FIG. 5, a flow diagram of a method to capture body movement related to a fixed coordinate system in accordance with one or more embodiments will be discussed. Method 500 as shown in FIG. 5 may include more or fewer blocks than shown in FIG. 5, and furthermore the blocks of method 500 may be arranged in various orders, and the scope of the claimed subject matter is not limited in this respect. In one or more embodiments, the origin 212 of global reference system 200 may be defined at block 510 as an initial origin of a tri-axial accelerometer sensor of user sensor 112. Next, the Y-axis of global reference system may be determined at block 512 as a unit vector in a direction opposite to the direction of gravity as measured by the tri-axial accelerometer sensor of user sensor 112. The X-axis may then be determined at block 514 as a cross product of the Y-axis and a magnetic filed vector as measured by a magnetometer sensor disposed in user sensor 112. The Z-axis may then be determined at block 516 from the cross product of the X-axis and the Y-axis. Once the global reference system 200 is defined, the orientation of one or more user sensors 112 may be determined at block 518. The orientation of the particular segment of user 210, for example the foot, calf, thigh, and so on, may also be determined based at least in part on the orientation of the user sensor 112 attached to the corresponding segment of user 210. As the user 210 moves within building 110, the kinematic variables of the movement of user 210 with respect to origin 212 of global reference system 200 may be determined at block 520, including for example acceleration, velocity, and/or displacement based on movement of the user 210 and/or the gait of user 210. The kinematic data captured by the one or more user sensors 112 may be broadcast to information handling system 116. In one or more embodiments, method 500 may be performed at least in part to perform an initial set up of global reference system 200 and/or calibration of user sensors 112. In some embodiments, the set up of global reference system 200 and/or calibration of sensors 112 may be periodically or occasionally performed by performing method 500 at least in part as needed. Furthermore, in some embodiments, the architectural features of building 110 and/or its contents such as furniture may be mapped to global reference system 200 so that the location of user 210 within building may be determined. For example, data regarding when user 210 moves from one room to another, how long user remains in a particular room, how frequently a user enters a particular room, and so on, may be captured via capturing the kinematic data as implemented by method 500, although the scope of the claimed subject matter is not limited in this respect.

Referring now to FIG. 6, a diagram of an information handling system capable of capturing capture body movement related to a fixed coordinate system in accordance with one or more embodiments will be discussed. Information handling system 600 of FIG. 6 may tangibly embody one or more of any of the network elements of network 100 as shown in and described with respect to FIG. 1. For example, information handling system 600 may represent the hardware of information handling system 116 and/or user sensors 112, with greater or fewer components depending on the hardware specifications of the particular device or network element. Although information handling system 600 represents one example of several types of computing platforms, information handling system 600 may include more or fewer elements and/or different arrangements of elements than shown in FIG. 6, and the scope of the claimed subject matter is not limited in these respects.

Some portions of the detailed description herein are presented in terms of processes, programs and/or symbolic representations of operations on data bits and/or binary digital signals within a computer memory, for example. These process descriptions and/or representations may include techniques used in the data processing arts to convey the arrangement of a computer system and/or other information handling system to operate according to such programs, processes, and/or symbolic representations of operations.

A process may be generally considered to be a self-consistent sequence of acts and/or operations leading to a desired result. These include physical manipulations of physical quantities. Usually, though not necessarily, these quantities take the form of electrical and/or magnetic signals capable of being stored, transferred, combined, compared, and/or otherwise manipulated. It may be convenient at times, principally for reasons of common usage, to refer to these signals as bits, values, elements, symbols, characters, terms, numbers and/or the like. However, these and/or similar terms may be associated with the appropriate physical quantities, and are merely convenient labels applied to these quantities.

The processes and/or displays presented herein are not inherently related to any particular computing device and/or other apparatus. Various general purpose systems may be used with programs in accordance with the teachings herein, or a more specialized apparatus may be constructed to perform the desired method. The desired structure for a variety of these systems will appear from the description below. In addition, embodiments are not described with reference to any particular programming language. It will be appreciated that a variety of programming languages may be used to implement the teachings described herein.

In one or more embodiments, a database may refer an organization of information created, stored, accessed, edited, and/or otherwise utilized by a computing platform. In one or more embodiments, a tag may refer to a command contained in a file, object, and/or document that may specify how the file, object, and/or document, and/or a portion thereof, may be formatted. In one or more embodiments, metadata may refer to information pertaining to data contained in a file, object, and/or document, for example formatting information, date of creation, date of editing, date saved, how data was obtained, and/or from where data was obtained. Such metadata, for example, may be utilized in for database management purposes and/or for data warehousing of multiple databases, although the scope of claimed subject matter is not limited in this respect. In one or more embodiments, an application programming interface (API) may refer to a set of routines, protocols, and/or tools utilized to cause a program to operate in conjunction with an operating system. In one or more embodiments, an operating system may refer to a program to execute on a computing platform to handle input and/or output commands, file management, printing, displaying, storing, and/or communicating of information for the computing platform. However, these are merely examples of database and/or operating system functions, and the scope of claimed subject matter is not limited in these respects.

In one or more embodiments, a hierarchical data set may refer to a set of data items, such as files and/or directories, organized hierarchically. For example a file system may be an example of a hierarchical data set. In one or more embodiments, metadata may refer to information about data items contained in a hierarchical data set or the like. For example, metadata may comprise a filename, a date of creation, an author and/or a set of keywords. Some metadata may reflect information specific to the type of item, for example width, height and/or orientation for a graphical document and/or tempo or key for an audio recording. In one or more embodiments, intrinsic metadata may refer to information about an item that may be associated to an item by its very nature. For example intrinsic metadata of an image may include width and/or height of the image. In one or more embodiments, extrinsic metadata may refer to information about an item associated by a user, such as a list of keywords, a rating or comments. However, these are merely examples of hierarchical data sets, metadata, intrinsic metadata, and/or extrinsic metadata, and the scope of the claimed subject matter is not limited in these respects.

In one or more embodiments, information handling system 600 may comprise one or more processors such as processor 610 and/or processor 612, which may comprise one or more processing cores. One or more of processor 610 and/or processor 612 may couple to one or more memories 616 and/or 618 via memory bridge 614, which may be disposed external to processors 610 and/or 612, or alternatively at least partially disposed within one or more of processors 610 and/or 612. Memory 616 and/or memory 618 may comprise various types of semiconductor based memory, for example volatile type memory and/or non-volatile type memory. Memory bridge 614 may couple to a graphics system 620 to drive a display device (not shown) coupled to information handling system 600.

Information handling system 600 may further comprise input/output (I/O) bridge 622 to couple to various types of I/O systems. I/O system 624 may comprise, for example, a universal serial bus (USB) type system, an IEEE 1394 type system, or the like, to couple one or more peripheral devices to information handling system 600. Bus system 626 may comprise one or more bus systems such as a peripheral component interconnect (PCI) express type bus or the like, to connect one or more peripheral devices to information handling system 600. A hard disk drive (HDD) controller system 628 may couple one or more hard disk drives or the like to information handling system, for example Serial ATA type drives or the like, or alternatively a semiconductor based drive comprising flash memory, phase change, and/or chalcogenide type memory or the like. Switch 630 may be utilized to couple one or more switched devices to I/O bridge 622, for example Gigabit Ethernet type devices or the like. Furthermore, as shown in FIG. 6, information handling system 600 may include a radio-frequency (RF) block 632 comprising RF circuits and devices, such as a baseband processor, media access controller, and/or an RF transceiver, for wireless communication with other wireless communication devices and/or via wireless networks such as network 100 of FIG. 1, for example where information handling system 600 embodies information handling system 116 and/or user sensors 112, although the scope of the claimed subject matter is not limited in this respect. In one or mole embodiments, RF block 632 may comprise circuits to implement various functions such as processing of baseband signals, although the scope of the claimed subject matter is not limited in this respect.

Although the claimed subject matter has been described with a certain degree of particularity, it should be recognized that elements thereof may be altered by persons skilled in the art without departing from the spirit and/or scope of claimed subject matter. It is believed that the subject matter pertaining to capturing body movement related to a fixed coordinate system and/or many of its attendant utilities will be understood by the forgoing description, and it will be apparent that various changes may be made in the form, construction and/or arrangement of the components thereof without departing from the scope and/or spirit of the claimed subject matter or without sacrificing all of its material advantages, the form herein before described being merely an explanatory embodiment thereof, and/or further without providing substantial change thereto. It is the intention of the claims to encompass and/or include such changes.

What is claimed is:
1. A method comprising:
defining a global reference system in which movement of a user may be determined;
defining an origin of the global reference system based on an orientation of a user sensor coupled to the user and on a location of an origin of a coordinate axis of the user sensor;
determining one or more kinematic variables based at least in part on movement of the user sensor with respect to the origin of the global reference system; and determining a health status of the user based on the one or more of the determined kinematic variables.

2. A method as claimed in claim 1, said defining a global reference system comprising determining a Y-axis as a unit vector in a direction opposite direction to gravity, determining an X-axis as a cross product of the Y-axis and a magnetic field vector, or determining a rotation about the X-axis, the Y-axis, or the Z-axis from a gravity vector and a magnetic field vector, or combination thereof.

3. A method as claimed in claim 1, wherein the defining the global reference system, the defining the origin of the global reference system, the determining the one or more kinematic variables, and the determining the health status of the user is performed by an information handling system remote from the user sensor.

4. A method as claimed in claim 1, further comprising receiving data on the one or more kinematic variables from the user sensor.

5. A method as claimed in claim 1, further comprising measuring one or more of walking speed, cadence, stride length, step length, step time, variation in step width, stride time, stance time, swing time, double support time, sway variability during stationary stance, or combinations thereof, based at least in part on one more of the kinematic variables.

6. A method as claimed in claim 1, further comprising measuring a time reference in which the kinematic variables are determined via a real-time clock.

7. A method as claimed in claim 1, further comprising determining one or more of acceleration, velocity, or displacement, or combinations thereof, based at least in part on one or more of the kinematic variables.

8. A method as claimed in claim 1, further comprising mapping a layout of a building to the coordinate system to determine a location of the user within the building based at least in part on the one or more kinematic variables.

9. An article of manufacture comprising a storage medium having instructions stored thereon that, if executed, result in:
defining a global reference system in which movement of a user may be determined;
defining an origin of the global reference system based on an orientation of a user sensor coupled to the user and on a location of an origin of a coordinate axis of the user sensor;
determining one or more kinematic variables based at least in part on movement of the user sensor with respect to the origin of the global reference system;
and
determining a health status of the user based on the one or more of the determined kinematic variables.

10. An article of manufacture as claimed in claim 9, said defining a global reference system comprising determining a Y-axis as a unit vector in a direction opposite direction to gravity, determining an X-axis as a cross product of the Y-axis and a magnetic field vector, or determining a rotation about the X-axis, the Y-axis, or the Z-axis from a gravity vector and a magnetic field vector, or combination thereof.

11. An article of manufacture as claimed in claim 9, further comprising an information handling system configured to execute the instructions stored on the storage medium.

12. An article of manufacture as claimed in claim 9, wherein the instructions, if executed, further result in:
receiving data on the one or more kinematic variables from the user sensor.

13. An article of manufacture as claimed in claim 9, wherein the instructions, if executed, further result in:
measuring one or more of walking speed, cadence, stride length, step length, step time, variation in step width, stride time, stance time, swing time, double support time, sway variability during stationary stance, or combinations thereof, based at least in part on one or more of the kinematic variables.

14. An article of manufacture as claimed in claim 9, wherein the instructions, if executed, further result in:
measuring a time reference in which the one or more kinematic variables are determined via a real-time clock.

15. An article of manufacture as claimed in claim 9, wherein the instructions, if executed, further result in:
determining one or more of acceleration, velocity, displacement, rotation, angular velocity, or angular acceleration, or combinations thereof, based at least in part on more or more of the kinematic variables.

16. An article of manufacture as claimed in claim 9, wherein the instructions, if executed, further result in:
mapping a layout of a building to the coordinate system to determine a location of the user within the building based at least in part on the one or more kinematic variables.

17. A kinematic sensor, comprising:
a tri-axial accelerometer sensor;
a gyroscope sensor; and
a magnetometer sensor;
said tri-axial accelerometer sensor, said gyroscope sensor, and said magnetometer sensor being coupled to a processor to determine one or more kinematic variables based at least in part on movement of the kinematic sensor by a user with respect to a fixed origin of a global reference system and to determine a walking speed, cadence, stride length, step length, step time, variation in step width, stride time, stance time, swing time, double support time, sway variability during stationary stance, or combinations thereof based on the one or more of the determined kinematic variables.

18. A kinematic sensor as claimed in claim 17, further comprising a radio-frequency transmitter and an antenna coupled to the radio-frequency transmitter to transmit the one or more kinematic variables to a remote information handling system.

19. A method comprising:
defining a global reference system in which movement of a user may be determined;
defining an origin of the global reference system based on an orientation of a user sensor coupled to the user and on a location of an origin of a coordinate axis of the user sensor; and
determining one or more kinematic variables based at least in part on movement of the user sensor with respect to the origin of the global reference system.

20. An article of manufacture comprising a storage medium having instructions stored thereon that, if executed, result in:
defining a global reference system in which movement of a user may be determined;
defining an origin of the global reference system based on an orientation of a user sensor coupled to the user and on a location of an origin of a coordinate axis of the user sensor; and
determining one or more kinematic variables based at least in part on movement of the user sensor with respect to the origin of the global reference system.

* * * * *